US000001344H

United States Statutory Invention Registration [19]

[11] Reg. Number: H1344

Baldauf et al.

[43] Published: Aug. 2, 1994

[54] PORTABLE AUTOMATIC SENSOR FOR TOXIC GASES

[75] Inventors: Frederick C. Baldauf; Brent R. Busey, both of Bel Air, Md.; Kenneth E. Thames, Aiken, S.C.

[73] Assignee: The United States of America as represented by the Secretary of the Army, Washington, D.C.

[21] Appl. No.: 767,755

[22] Filed: Sep. 30, 1991

Related U.S. Application Data

[63] Continuation-in-part of Ser. No. 594,456, Oct. 9, 1990, abandoned.

[51] Int. Cl.[5] ..... C12Q 1/46

[52] U.S. Cl. ..... 435/20

[58] Field of Search ..... 422/82.07, 82.08; 436/103, 104, 172; 435/4, 18–20, 183, 184, 817

[56] References Cited

U.S. PATENT DOCUMENTS

| | | | |
|---|---|---|---|
| 4,071,020 | 1/1978 | Pugliese | 128/2 A |
| 4,447,546 | 5/1984 | Hirschfeld | 436/527 |
| 4,861,727 | 8/1989 | Hauenstein et al. | 436/136 |

*Primary Examiner*—Robert L. Stoll
*Assistant Examiner*—Joseph D. Anthony
*Attorney, Agent, or Firm*—Anthony T. Lane; Edward Goldberg; Michael Sachs

[57] ABSTRACT

A method is provided for the integration of a low-volume liquid flow and mixing system and a portable optical waveguide-based fluorescence detector for the chemical analysis of reagents in fluorescence-based reactions. The method is particularly applicable to the detection of enzyme inhibitors, modifiers, or ligands in cases where a fluorescent enzyme substrate or product exists. In a preferred embodiment, the presence and concentration of acetylcholinesterase inhibitors, such as chemical warfare nerve agents or certain insecticides, is determined by mixing aqueous samples with a dilute solution of n-methyl indoxyl acetate, and monitoring the formation of a fluorescent product (n-methyl indoxyl). The presence of an acetylcholinesterase inhibitor reduces the amount of fluorescent product formed in a given time period. The reaction product passes through a flow cell in which it is excited by the evanescent wave produced by light as the light undergoes total internal reflection within an optical rod or fiber, or by light coming out the end-face of an optical fiber or rod.

6 Claims, 3 Drawing Sheets

A statutory invention registration is not a patent. It has the defensive attributes of a patent but does not have the enforceable attributes of a patent. No article or advertisement or the like may use the term patent, or any term suggestive of a patent, when referring to a statutory invention registration. For more specific information on the rights associated with a statutory invention registration see 35 U.S.C. 157.

OPTICAL WAVEGUIDE-OPTICAL SCHEMATIC

FLOW CELL DESIGNS

PORTABLE AUTOMATIC SENSOR FOR TOXIC GASES

GOVERNMENTAL INTEREST

The invention described herein may be made, used or licensed by or for the Government for governmental purposes without the payment to us of any royalties thereon.

CROSS-REFERENCE TO RELATED APPLICATION

This application is a continuation-in-part of copending application, Ser. No. 07/594,456, filed Oct. 9, 1990, now abandoned.

BACKGROUND OF THE INVENTION

This invention relates generally to chemical analysis, and more particularly to a method for using a portable automatic sensing device for the detection of acetylcholinesterase inhibitors.

More specifically, the invention consists of the combination of a method involving liquid flow chemistry with fluorescence detection applied to the chemical analysis of very small sample volumes of acetylcholinesterase inhibitors.

PRIOR ART

The major design of the liquid flow and mixing system is considered to be prior art. The specific chemical reaction used in the preferred embodiment has been previously published (Guilbault, G., Sader, M., Glazer, R., Skou, C., Analytical Letters, 1(6), p. 365, 1968). With regard to the fluorescence sensor itself, prior, art is disclosed in U.S. Pat. No. 4,447,546, issued May 8, 1984 to Tomas E. Hirschfeld for "Fluorescent Immunoassay Employing Optical Fiber in Capillary Tube," and in U.S. Pat. No. 4,558,014.

These patents describe an apparatus and method for fluorescently-labeled immunoassays. In these assays, totally-internally reflected light conducted through an optical fiber or rod excites fluorescence in antibody-antigen complexes formed at or near the surface of the optical fiber or rod. The electromagnetic energy probing the space without the optical fiber or rod is termed the evanescent wave, and extends only a few hundred angstroms into the optically-rarer medium surrounding the fiber or rod. Because the evanescent wave only probes a very thin layer of sample surrounding the optical fiber or rod, this method has the capability of analyzing very small volumes of sample.

The specific and novel combination and application of otherwise previously disclosed technologies is an object of this invention.

A problem frequently encountered in the detection of toxic gaseous compounds in a small hand-portable device is an inability to attain adequate sensitivity while maintaining small size, low weight and simple design. The sensitivity of the detector depends on the sampling time (or volume sampled), sampling efficiency, the sensitivity of the physical or chemical phenomenon being exploited for detection and transduction, and the magnitude of noise and non-specific interactions affecting sensor output.

In existing detectors, sensitivity is attained at the expense of response time or duration of the monitoring. For example, in some existing methods of monitoring of toxic gases, a volume of air is exposed to a solid phase collector over some given period of time and then is quantitated at the end of the time period.

While these detectors can give sensitive readings of toxic gases, there is a significant time delay before a quantitative reading is obtained. Other monitoring systems, while giving sensitive results in a reasonable time period, can only be used once and then must be discarded.

Existing monitoring methods routinely require expensive laboratory procedures involving sample transport or preparations of samples for assay.

Rapid analysis of gaseous toxic materials in the areas of food and water analysis, environmental monitoring, and industrial settings is a problem that continues to exist and is currently addressed by time-consuming expensive methods or by techniques that may be described as inadequate.

Many problems associated with exposure to toxic materials could be avoided or minimized by a detection procedure which gives near "real-time" indication of the presence of toxic gases. Equally important are the characteristics of economy, small size, and ease of use for the successful application of such devices.

THE INVENTION

The present invention is particularly applicable to the detection of enzyme inhibitors, modifiers, or ligands in cases where a fluorescent enzyme substrate or product exists.

In a preferred embodiment of the invention, acetylcholinesterase acts on n-methyl indoxyl acetate to form a fluorescent product, n-methyl indoxyl. The presence of an acetylcholinesterase inhibitor, such as chemical warfare nerve agents or certain insecticides, reduces the amount of fluorescent product formed in a given time period.

The reaction product is excited by the evanescent wave or by light coming out the end-face of an optical fiber or rod. Fluorescence is captured by the optical fiber or rod and conducted to a photodetector (photodiode or photomultiplier tube).

The liquid flow system used in conjunction with the detector is constructed and functions as follows. Analyte in aqueous solution is mixed with an aqueous solution of acetylcholinesterase in a transfer line, with or without the assistance of special mixing interpositions. This solution, after an adequate incubation time, is then mixed with a solution of the enzyme substrate, n-methyl indoxyl acetate, in a subsequent segment of transfer line (with or without a special mixing interposition).

This final mixture is then passed by the optical fiber or rod (held in a specially-designed flow cell) of the detector. The magnitude of the fluorescent signal is compared to the magnitude of the signal when no analyte is present in the sample solution, the fluorescence signal being inversely proportional to the enzyme inhibitor concentration.

A portable system such as that described has been demonstrated to detect very low concentrations of acetylcholinesterase inhibitors in a sample volume of only 0.15 ml., in a total assay time of only two minutes. The system was capable of running repetitive assays at the rate of 30/hour for extended periods of time. The unique integration of continuous enzyme-based sensing with a small portable fluorescence detector forms the basis of the current invention. Current data demonstrate sensitivity and response times not achievable by existing portable sensors or monitors, for this application.

In an alternative mode of operation of the invention, the enzyme can be immobilized directly onto the optical fiber element providing certain advantages. With an enzyme, such as acetylcholinesterase, immobilized on the surface of the fiber, pesticides could be introduced directly into the non-fluorescent n-methyl indoxyl acetate reagent stream.

The sample slug is moved directly to the optical fiber containing the immobilized acetylcholinesterase. Reaction times would be short, on the order of a minute, followed by exposure of the optical fiber containing the immobilized enzyme to a slug of the n-methyl indoxyl acetate or other suitable reagent.

If the sample contains pesticide or other enzyme inhibiting compound, binding to the enzyme would occur, thus rendering it inactive, and thus eliminating the fluorescence-generating reaction.

If the sample does not contain pesticide, the enzyme would remain active, thus providing the fluorescence-generating reaction. Immobilizing the enzyme directly onto the fiber would conserve enzyme and improve sensitivity and response time. This mode of operation may be best suited to dosimeter monitoring operations to ascertain accumulated dose.

Alternatively, the enzyme can be immobilized within a disposable cartridge upstream to the optical fiber. With this configuration, when the enzyme is used up it can be easily replaced.

OBJECTS OF THE INVENTION

A principal object of this invention is to provide a novel method of combining a portable fluorescence detector and sample flow and mixing apparatus for the detection of fluorescent substances or substances capable of forming or inhibiting the formation of fluorescent substances.

A further object of this invention is to provide a method for the detection of toxic acetylcholinesterase inhibitors (including chemical warfare nerve gases and certain pesticides) in aqueous solution.

DESCRIPTION OF THE DRAWINGS

These and other objects and attendant advantages of this invention will become more obvious and apparent from the detailed specification and accompanying drawings in which.

DESCRIPTION OF THE PREFERRED EMBODIMENTS OF THE INVENTION

Figure 1:
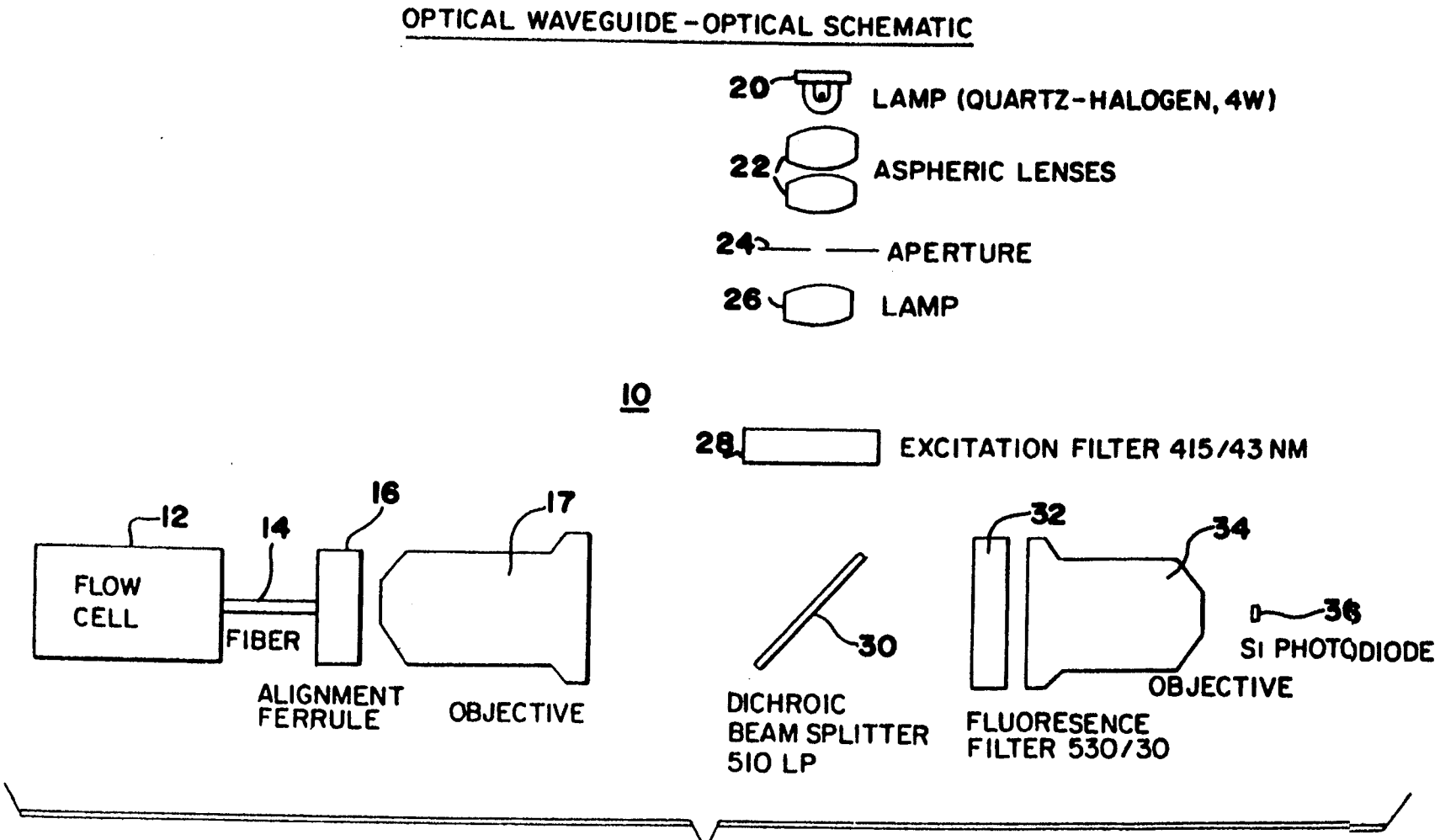
FIG. 1 is an optical schematic of an optical waveguide fluorescence detector.

Referring now to FIG. 1, there is shown an optical schematic of an optical waveguide system 10. The optical elements are arranged similarly to an epi-illumination fluorescence microscope, only with fixed positioning. The objective arm of the waveguide system 10 consists (going from left to right) of a flow cell 12 connected by a fiber 14 to an alignment ferrule 16 having an objective lens 17 spaced therefrom.

A second arm of the waveguide system, arranged normal to the objective arm supplies excitation light from an incandescent lamp 20. Light from the lamp 20 is collected and focussed by a pair of aspheric lenses 22. The light then passes through an aperture 24, another aspheric lens 22, and an excitation filter 28 (415/43 nm in the preferred embodiment).

Filtered excitation light then impinges on a long-pass dichroic beam splitter 30 (510 nm), where it is reflected into the objective arm. Fluorescence collected through the optical fiber 14 passes back through the objective arm, passes through the dichroic beam splitter 30, through a fluorescence filter 32 (530/30 nm), through an objective lens 34 to a silicon photodiode 36.

Figure 2:
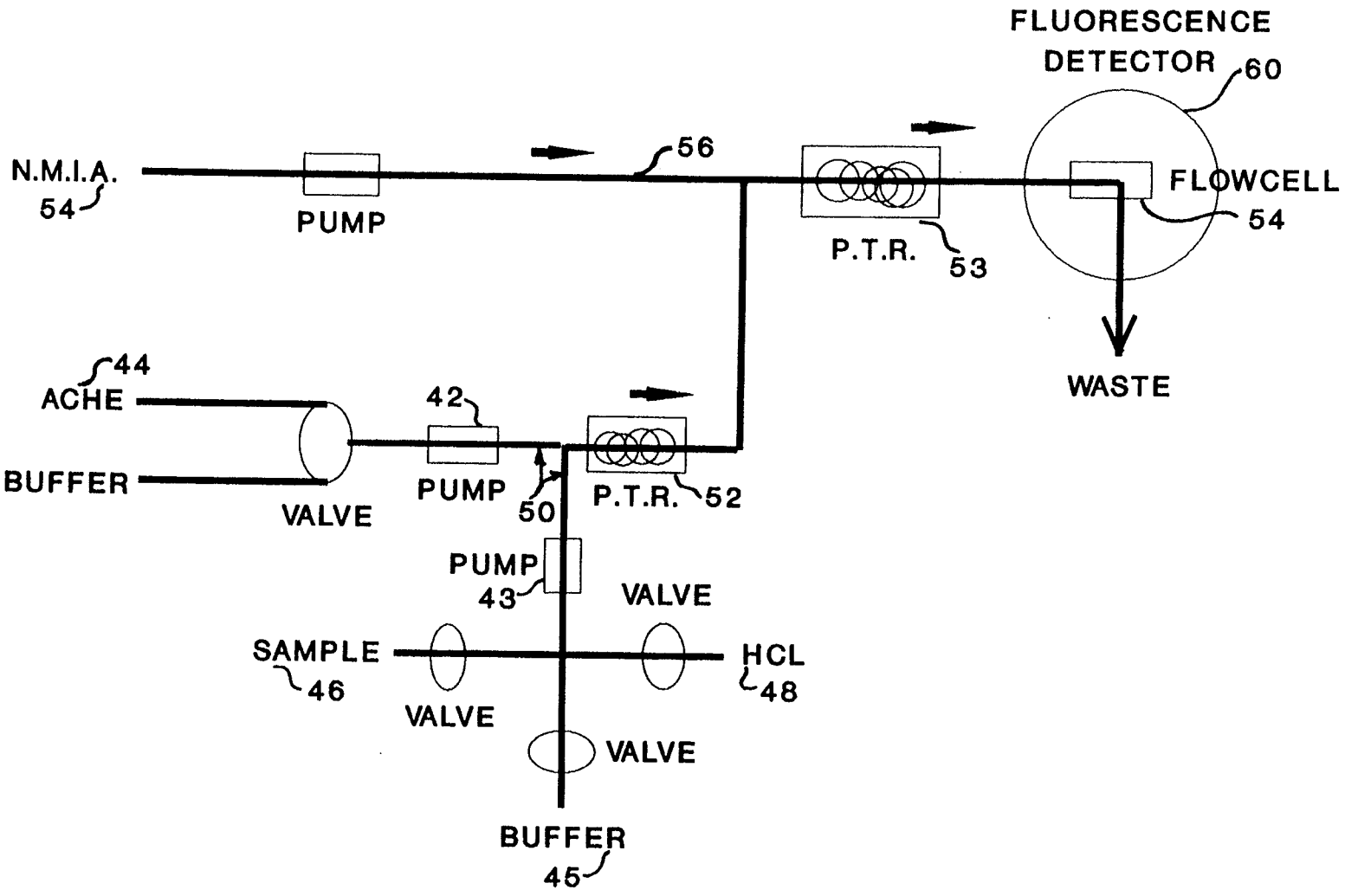
FIG. 2 is a line drawing of an automated liquid flow and mixing system, interfaced with a fluorescence detector.

FIG. 2 shows a liquid reagent flow and mixing apparatus (inclusive of 42–54) interfaced to a fluorescence detector 60. Pumps 42 and 43 are used to pump an acetylcholinesterase enzyme solution (ACHE, 44), and either buffer 45, sample 46 or hydrochloric acid (HCl, 48, for cleaning) through tubing 50 in the direction indicated, into a packed tube reactor, mixing coil or tube segment (P.T.R., 52) held in a thermostated bath (not shown). Any acetylcholinesterase inhibitors present in the sample bind to the enzyme during passage through this portion of the system.

A solution of n-methyl indoxyl acetate (N.M.I.A., 54) is pumped through line 56, mixed with the sample/enzyme solution and passed through a second packed tube reactor, mixing coil or tube segment (P.T.R., 53) in a thermostated bath (not shown). During this stage, active enzyme hydrolyzes the N.M.I.A. 54, producing a fluorescent product. The concentration of fluorescent product is inversely related to the concentration of toxic analyte (acetylcholinesterase inhibitor) present in the sample.

The mixture passes through a flow cell 54 integral to an optical waveguide-based fluorescence detector 60 which monitors the intensity of the collected fluorescent light at a band around 530 nm.

By periodically switching from sample 46 to buffer 45, one can confirm the signal obtained with full enzyme activity (establishing a baseline response). The length of time required to return to maximum enzyme activity after switching to buffer can also quantitate sample concentrations which are too high to fall in the normal quantitative range of the primary inhibitory reaction.

Figure 3:
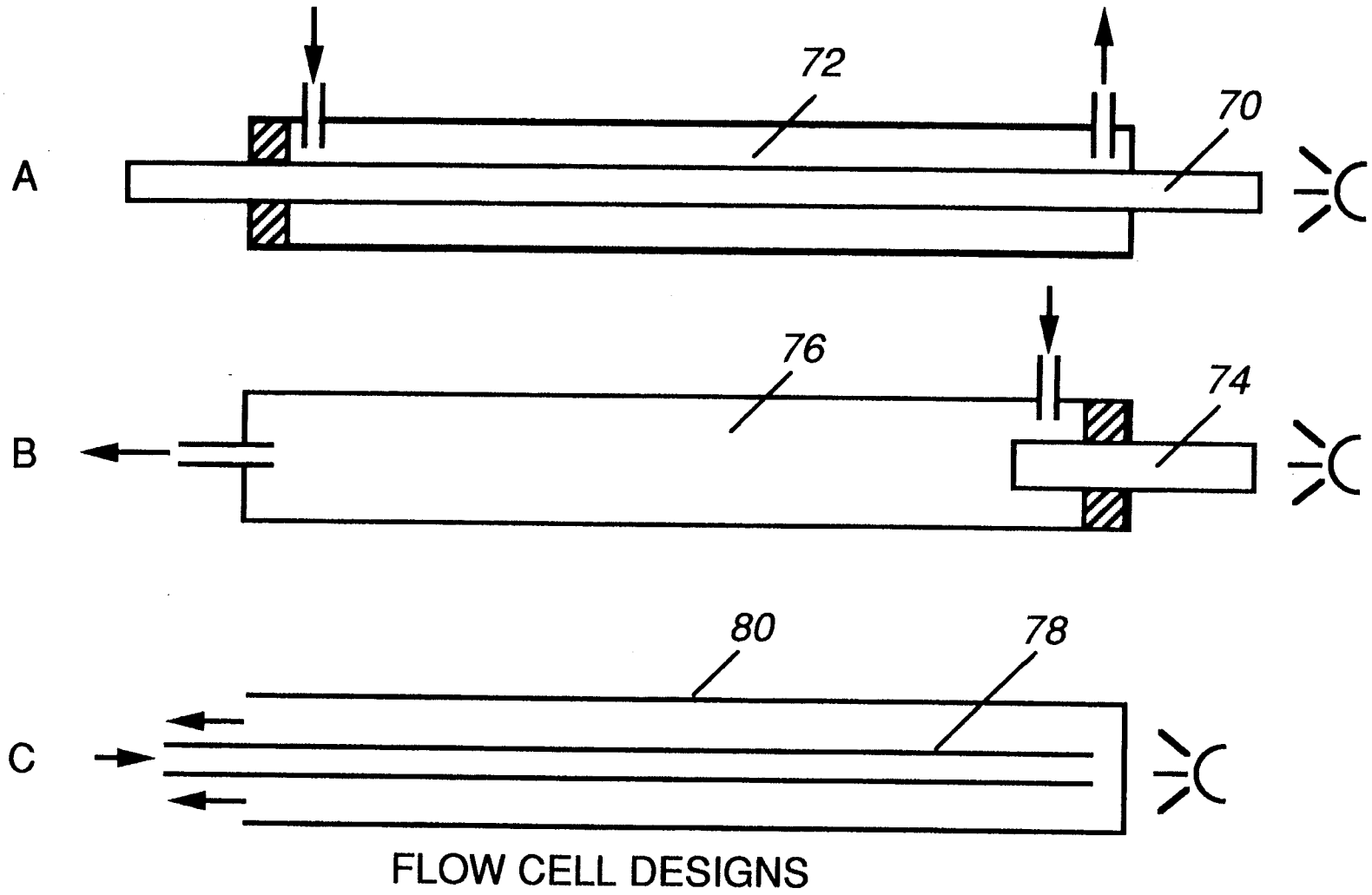
FIG. 3 shows various designs of the flow cell in which the fluorescent product is detected.

FIG. 3 illustrates three possible designs for the flow cell (which is denoted as 12 in FIG. 1 and 54 in FIG. 2). The actual method of sample excitation is determined by the construction of the flow cell. In design A, light undergoes total internal reflection at the rod/solution interface, as the light passes through a quartz rod 70 held in a concentric hollow tube 72. Fluorophores within a distance of about 100 nm of the rod surface can be excited with the evanescent energy of the totally-reflected light. Some of the fluorescence produced by these absorbers is captured back into the fiber and can be detected. In design B, the bulk of the fluorescence detected is produced by the excitation light exiting the end of a short quartz or plastic rod 74 which extends a short distance into a hollow flow cell 76, illuminating fluorophores in the bulk solution. This implementation is commonly referred to as an "optrode." Design C consists of a thin open-ended capillary tube 78 placed within (and extending to the end of) a slightly larger closed-ended capillary tube 80. Solution is pumped through the center tube and exits via the concentric outer tube. Both the inner and the outer tubes serve as optical waveguides, but the exact optical properties of this model have not yet been studied by the patent applicants. The fluorescent signal obtained from a standard solution is about 150 times as high with design B as with design A. Design C has an advantage in that it has a smaller dead volume and is less prone to trapping air bubbles. It has a sensitivity near that of design B, and could probably be engineered to have a sensitivity up to 3 times as high as design B. The agent data presented here was obtained using design B.

In the preferred embodiment, a hand portable automatic analysis system can be constructed which is capable of monitoring acetylcholinesterase inhibitors continuously for long periods of time, with readings being taken every one to two minutes and with extremely high sensitivity and fast response time.

It is to be noted that while fluorescence detection is well known as a sensitive analytical technique in the laboratory, methods for employing it in an industrial or field setting have been limited. The unique integration of continuous enzyme-based sensing with a small portable fluorescence detector forms the basis of this invention. Current data demonstrates sensitivity and response times not achievable by existing portable sensors or monitors.

In an alternative mode of operation of this invention, the enzyme can be immobilized directly onto the optical fiber 14 of FIG. 1, thus providing certain advantage. With an enzyme, such as acetylcholinesterase, immobilized on the surface of the fiber 14, a sample slug can be reacted directly with the optical fiber 14 containing the immobilized acetylcholinesterase. Reaction times would be short, on the order of a minute, followed by exposure of the optical fiber 14 containing the immobilized enzyme to a slug of the n-methyl indoxyl acetate or other suitable reagent.

If the sample contains a pesticide or other enzyme inhibiting compound, binding to the enzyme would occur, rendering it inactive, and thus eliminating the fluorescence-generating reaction.

If the sample does not contain an acetylcholinesterase inhibitor, the enzyme would remain active, thus allowing the fluorescence-generating reaction to proceed.

Immobilizing the enzyme directly onto the fiber 14 could conserve enzyme and improve sensitivity and response time. This mode of operation may be best suited to dosimeter monitoring operations to ascertain accumulated dose. Alternatively, the enzyme can be immobilized within a disposable cartridge upstream of the optical fiber 14. With this configuration, when the enzyme is used up it can be easily replaced.

EXPERIMENTAL PROCEDURES DETAILS

Typical assay reagents were prepared as follows. A concentrated methyl cellosolve solution of N-methyl indoxyl acetate (NMIA) was diluted with 10 mM acetate buffer (pH 5.2) to a concentration of 0.19 mM. Electric eel acetylcholinesterase (Sigma) was diluted to a nominal activity of 0.02 units/liter in 100 mM phosphate buffer (pH 7.0). BRIJ-35 surfactant was added to the enzyme solution, to a concentration of 0.02%. Agent samples were made by diluting stock solutions with distilled water. Hydrochloric acid (0.1M) was used to periodically rinse adsorbed reagents from the flow systems. A phosphate buffer solution (0.1M) was used for rinsing and as a blank sample. L- This buffer also contained casein (0.1%, for blocking adsorption of the enzyme to the packed-tube reactors) and sodium azide (0.01%).

A drift in background signal over time was virtually eliminated through two procedures: 1) the NMIA substrate was dissolved in an acetate buffer (pH 5.2), resulting in slower unassisted hydrolysis than occurred in a neutral buffer; and 2) 0.1 M HCl was used to periodically rinse the reagent lines to remove adsorbed enzyme or substrate. The latter rinsing was effective when done for 60 seconds every three minutes.

The solenoid valves and multichannel peristaltic pump used in the fluid handling system were actuated via an electronic interface to a TRS80 portable microcomputer. Short lengths of 0.5 mm I.D. Teflon tubing were packed with 0.25 mm glass beads, to serve as mixing coils and reactors (packed-tube reactors). All tubing was Teflon, except for connections, pump tubing and pinch valve tubing, which were all composed of silicone rubber. Relative signal levels (uninhibited enzyme) were determined at different flow rates and with different periods of incubation (stopped flow). These results and a desire to minimize reagent consumption, reaction time and sample size, led to a choice of reaction conditions. Flow rate was set at 0.66 ml/min, with a sample size of 0.15 ml and a stopped flow incubation period of 80 seconds. Agent samples were analyzed alternately with the analysis of a blank. Each separate analysis (of sample or of the blank) required 160 seconds total time, which included sample aspiration, mixing with enzyme, mixing with substrate, incubation, and passage through the optical waveguide fluorescence detector. Using these parameters, total reagent consumption was approximately 0.33 ml/min.

CONCLUSIONS

A bench-top analyzer was assembled capable of detecting acetylcholinesterase inhibiting nerve agents down to an aqueous concentration of 0.2 ng/ml or less. The same reagents were used in a smaller low reagent volume system linked to a small, portable detector (the fiber optic waveguide). The latter system was capable of detecting nerve agents at an aqueous concentration of 1.0 ng/ml, with a total reagent consumption rate of only 0.33 ml/min. This indicates the utility of the fiber optic waveguide for chemical agent detection, in addition to its previously shown utility in the detection of biological threat agents. It also indicates the feasibility of using a continuous enzyme stream for continuous or repetitive assays of acetylcholinesterase inhibitors.

Since these and certain other changes may be made in the above described apparatus and process without departing from the scope of the invention herein involved, it is intended that all matter contained in the above description or shown in the accompanying drawings shall be interpreted in an illustrative and not a limiting sense.

Obviously, many modifications and variations of the present invention are possible in light of the above teachings. It is, therefore, to be understood that within the scope of the appended claims, the invention may be practiced otherwise than as specifically described.

What is claimed is:

1. A method for the analysis of an aqueous sample for the presence of acetylcholinesterase inhibitors consisting essentially of simultaneously:

monitoring the presence and concentration of an acetylcholinesterase inhibitor by measuring the fluorescence of a chemical in an acetylcholinesterase-mediated reaction;

carrying out the reaction in an automated reagent flow and mixing apparatus with small volumes of reagents; and measuring the concentration of said chemical in solution by an optical fiber or rod through which the emitted fluorescent light travels to an optical detector.

2. The method of claim 1 wherein said chemical is a product of the reaction.

3. The method of claim 1 wherein said chemical is a reactant of said acetylcholinesterase-mediated reaction.

4. The method of claim 1 wherein said reaction occurs in said apparatus.

5. The method of claim 1 wherein said reaction occurs on the surface of an optical fiber of said apparatus.

6. The method of claim 5 wherein said reaction occurs adjacent to said surface of said fiber.

* * * * *